(12) United States Patent
Khaze Harry

(10) Patent No.: US 8,117,698 B1
(45) Date of Patent: Feb. 21, 2012

(54) DIAPER CHANGING SYSTEM

(76) Inventor: Zaida Khaze Harry, Palisades Park, NJ (US)

(*) Notice: Subject to any disclaimer, the term of this patent is extended or adjusted under 35 U.S.C. 154(b) by 0 days.

(21) Appl. No.: 12/912,046

(22) Filed: Oct. 26, 2010

(51) Int. Cl.
*B68G 5/00* (2006.01)
*A47C 16/00* (2006.01)
*A47G 9/02* (2006.01)
*A41B 13/06* (2006.01)
*A41B 9/00* (2006.01)
*A41B 13/08* (2006.01)
*A41D 11/00* (2006.01)
*A61F 5/37* (2006.01)

(52) U.S. Cl. ............... 5/655; 5/494; 2/69.5; 2/75; 2/80; 2/111; 128/872; 128/874

(58) Field of Classification Search .............. 5/655, 417, 5/420, 922, 923, 494; 2/69.5, 111, 75, 80; 128/845, 869–874
See application file for complete search history.

(56) References Cited

U.S. PATENT DOCUMENTS

| | | | |
|---|---|---|---|
| 1,573,446 A * | 2/1926 | Popham | 128/874 |
| 3,987,505 A | 10/1976 | Hickey | |
| 4,202,052 A | 5/1980 | Bilanzich | |
| 5,345,627 A * | 9/1994 | Cammarata | 5/419 |
| 6,009,874 A | 1/2000 | Sartin et al. | |
| 6,499,165 B1 | 12/2002 | Morgillo | |
| 6,681,422 B2 | 1/2004 | Landry | |
| 6,708,356 B1 * | 3/2004 | LaValle | 5/655 |
| 6,755,198 B2 | 6/2004 | Parker | |
| 6,834,405 B1 | 12/2004 | Hillstead | |
| 2005/0236002 A1* | 10/2005 | Cooley | 128/845 |

* cited by examiner

*Primary Examiner* — Jonathan Liu
(74) *Attorney, Agent, or Firm* — Goldstein Law Offices, P.C.

(57) ABSTRACT

A system of placing a vest with a rear hook and loop fastener on an infant, laying the child on a changing pad having a surface hook and loop fastener, and attaching the vest to the changing pad by fastening the hook and loop fasteners together, securely holding the infant onto a changing pad while changing a diaper. The changing pad has a flap that when closed, covers the surface hook and loop fastener when the system is not in use, to prevent snagging other clothing. The vest that can be placed on the child prior to and in preparation for changing a diaper when the child is standing, seated upright, or lying down. The vest has a front hook and loop closure for easy opening and closing by the user. The vest optionally includes tethered toys to amuse the child during diaper changing.

4 Claims, 4 Drawing Sheets

DIAPER CHANGING SYSTEM

CROSS-REFERENCE TO RELATED APPLICATIONS

Not applicable.

BACKGROUND OF THE INVENTION

The invention relates generally to a system to securely hold an infant onto a changing pad while changing a diaper. More particularly, the invention relates to a system of placing a vest with a rear hook and loop fastener on a young child, laying the child on a changing pad having a surface hook and loop fastener, and attaching the vest to the changing pad by fastening the hook and loop fasteners together, securely holding an infant on a changing pad while changing a diaper.

Infants and toddlers are always "on the go" once they discover how to move, squirming, rolling-over, crawling and walking. Their world expands with their new skills and they are eager to be in motion when they are not eating or sleeping. As parents know, these children hate to be interrupted in their investigations. While they are developing and growing, generally they are not yet sufficiently developed to be toilet trained and must wear diapers. Diaper changing is an interruption. They do not like to lie still for the procedure. They twist and turn to break free of their caretaker's grasp. The caretaker desires to change the diaper at a convenient height for his or her back and places the child on a changing table or a platform for the process. The child's efforts to break free by twisting and rolling can result in the child falling off the table or platform, further resulting in serious injury. Even if the child is lying on the floor, the twisting and rolling can results in feces spreading over the child, the child's clothes, the changing pad, and even the parent. The squirming makes diaper changing a struggle of wills between parent and child.

Changing tables have belts that strap over the waist or shoulders of the child. Generally these belts do not hold the child tightly and the child can twist and squirm out of the waist belt in particular. Others have proposed different forms of upper body restraints, such as a two-piece tank top that has a back piece permanently attached to the changing table.

Restraining a child on a flat surface is similar to restraining a patient on a bed. Some have suggested a mattress cover with a vest front sewn directly onto the mattress cover. Others have designed a sleeper sack or jacket that is attached directly onto a crib sheet to prevent the child from kicking the covers off and moving around in a crib. The sleeper sack would interfere with diaper changing since the child's legs are restrained inside the sleeper. Some have proposed restraints that extend between the legs which would interfere with diaper changing.

While these units may be suitable for the particular purpose employed, or for general use, they would not be as suitable for the purposes of the present invention as disclosed hereafter.

SUMMARY OF THE INVENTION

It is an object of the invention to produce a system to securely hold an infant on a changing pad while changing a diaper. Accordingly, the system has a changing pad with a surface hook and loop fastener to attach an article of clothing that the infant is wearing.

It is a further object of the invention to produce a system to securely hold an infant on a changing pad while changing a diaper. Accordingly, the system has an attachable vest with a hook and loop fastener on the rear to attach to a surface hook and loop fastener on the changing pad.

It is another object of the invention to produce a system to securely hold an infant on a changing pad with an article of clothing that can be placed on a child when the child is in any position, in preparation for changing a diaper. Accordingly, the system has a changing pad and an attachable vest that can be placed on the child prior to and in preparation for changing a diaper when the child is standing, or seated upright, or lying down.

It is yet a further object of the invention to produce a system to securely hold an infant on a changing pad with an article of clothing that is easily and quickly opened and closed by a user having a pair of hands. Accordingly, the system has a changing pad and an attachable vest with a front hook and loop fastener closure having a pair of strips, the hook and loop fastener not requiring an exact matching of the strips to effectively close the vest, so that the vest is closed or opened quickly and easily with one hand of the user.

It is yet another object of the invention to produce a system to securely hold an infant on a changing pad with a hook and loop fastener that does not snag an article of clothing when not in use. Accordingly, the system has a changing pad with a protective flap to cover a hook and loop fastener when not in use.

The invention is a system of placing a vest with a rear hook and loop fastener on an infant or small child, laying the child on a changing pad having a surface hook and loop fastener, and attaching the vest to the changing pad by fastening the hook and loop fasteners together, securely holding an infant or a toddler onto a changing pad while changing a diaper. The changing pad has a flap that when closed, covers the surface hook and loop fastener when the system is not in use to prevent snagging other clothing. The vest that can be placed on the child prior to and in preparation for changing a diaper when the child is standing, seated upright, or lying down. The vest has a front hook and loop closure for easy opening and closing by the user. The vest optionally includes tethered toys to amuse the child during diaper changing.

To the accomplishment of the above and related objects the invention may be embodied in the form illustrated in the accompanying drawings. Attention is called to the fact, however, that the drawings are illustrative only. Variations are contemplated as being part of the invention.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 3:
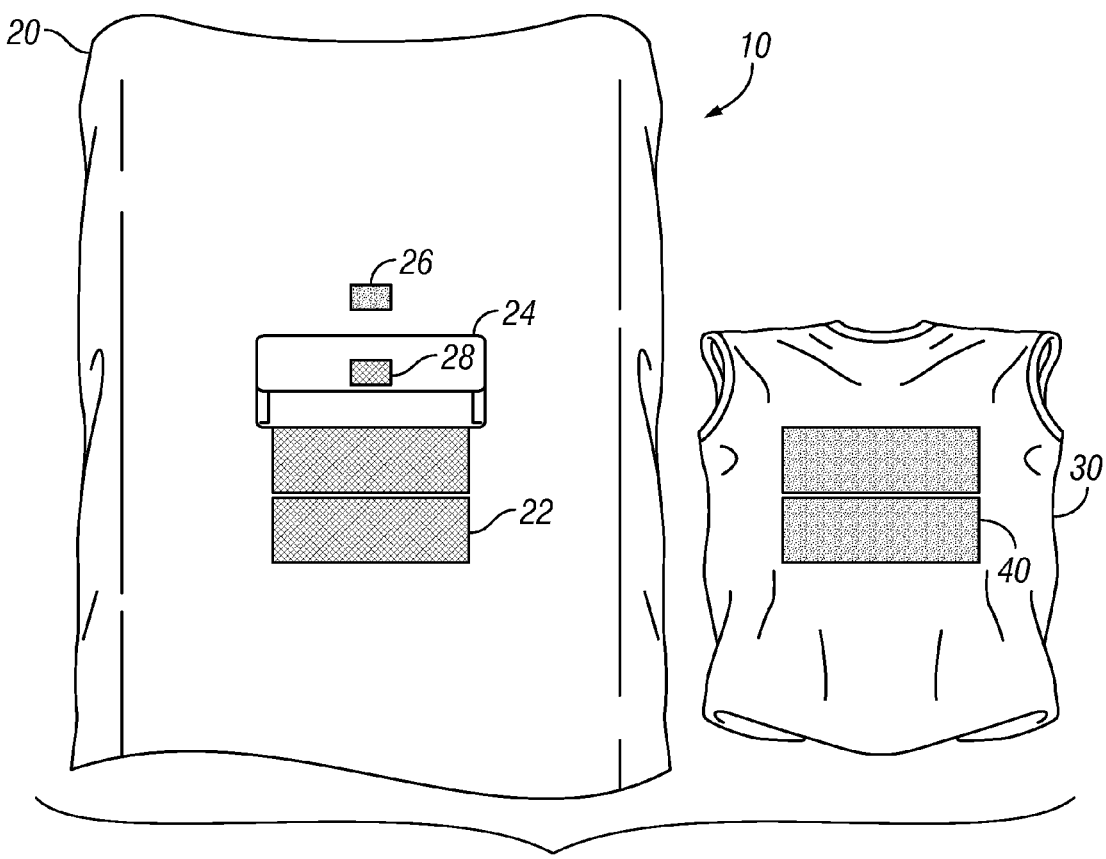
FIG. 3 is a top plan view of the system to securely hold an infant or a toddler, separately showing the top surface of the changing pad and the rear of the vest, both with the hook and loop fasteners.

FIG. 3 illustrates a system 10 to securely hold an infant onto a changing pad 20 while changing a diaper. The system 10 is made up of a vest 30 affixed with a rear hook and loop fastener 40 and the changing pad 20 having a surface hook and loop fastener 22 affixed. The user places the vest 30 on the infant, lays the infant down supine on the changing pad 20 and attaches the vest 30 to the changing pad 20 by fastening the hook and loop fasteners 22, 40 together, securely holding the infant onto the changing pad 20 when changing a diaper. The infant is restrained from turning over or falling off a changing table or other platforms used for diaper changing.

Figure 1:
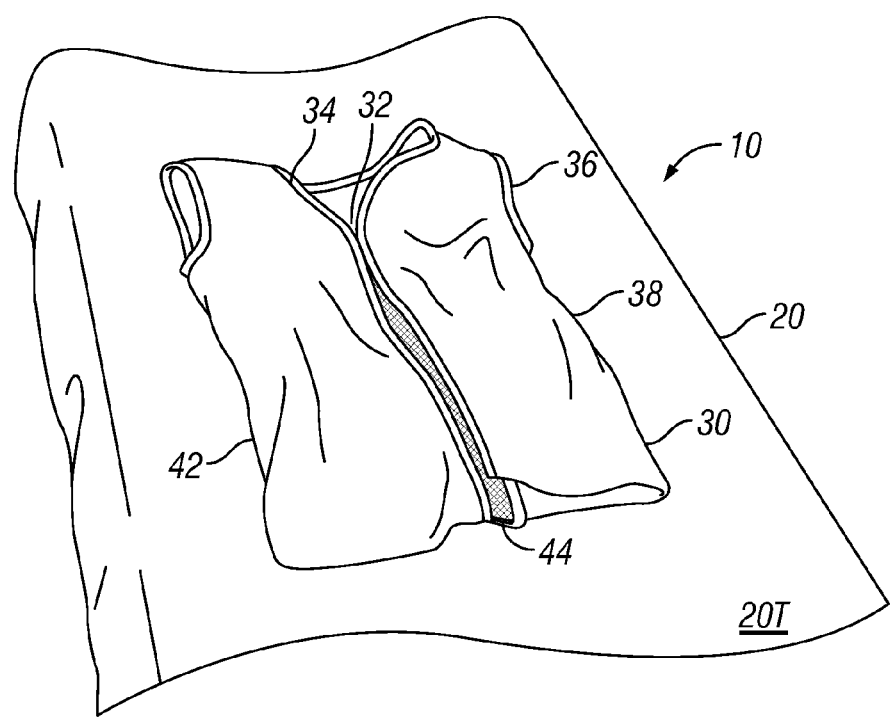
FIG. 1 is a diagrammatic perspective view from the top of an assembled system to securely hold an infant onto a changing pad while changing a diaper, made up of a vest having a rear hook and loop fastener and a changing pad having a surface hook and loop fastener.

FIG. 1 shows an assembled system 10 to securely hold an infant onto a changing pad 20 with the vest 30 secured to the changing pad 20. The vest 30 has a front with an opening in the front which is closed when placed on the infant. The vest 30 has a neck opening 34, and a pair of arm openings 36 and a rear 42 which is joined to the front 38. The changing pad 20 has a top surface 20T and the vest 30 is secured to the top surface 20T of the changing pad 20.

Figure 2:
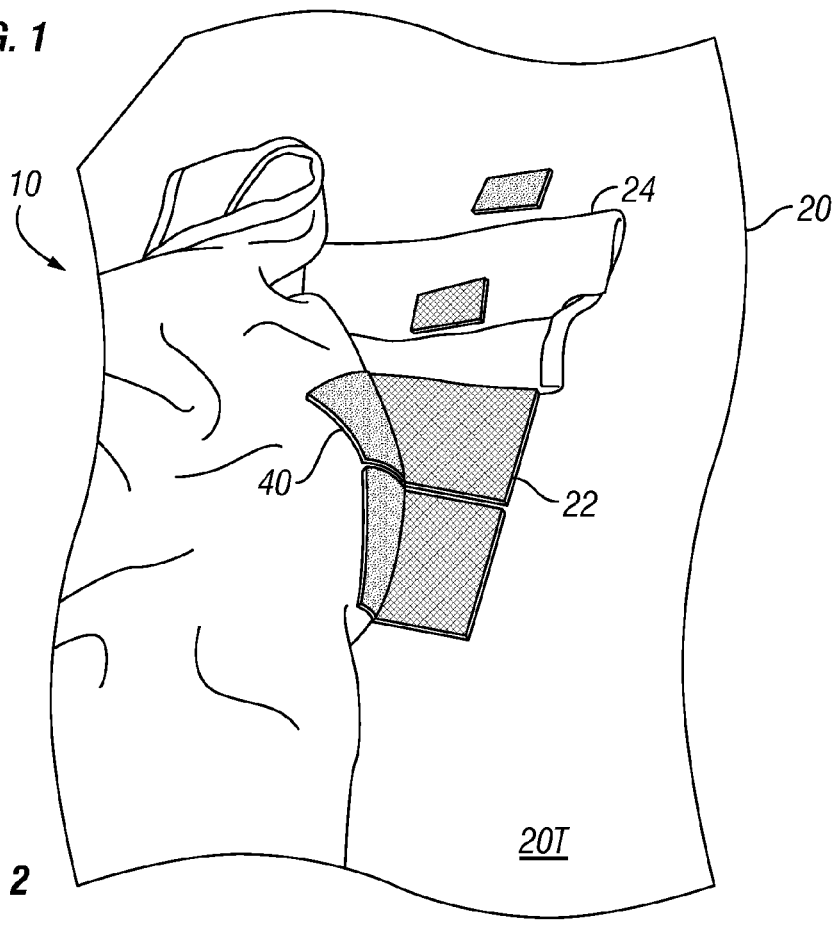
FIG. 2 is a diagrammatic perspective view from the top of the vest having a rear hook and loop fastener partially peeled away from the changing pad having a surface hook and loop fastener.

FIG. 2 shows the vest 30 attaching to the changing pad 20. The rear hook and loop fastener 40 is fixed on the rear 42 of the vest 30 and is mated to the hook and loop fastener 22 fixed on the changing pad 20. A flap 24 covers the hook and loop fastener 22 on the changing pad 20 when the hook and loop fastener 22 is not engaged with the vest 30.

Figure 4:
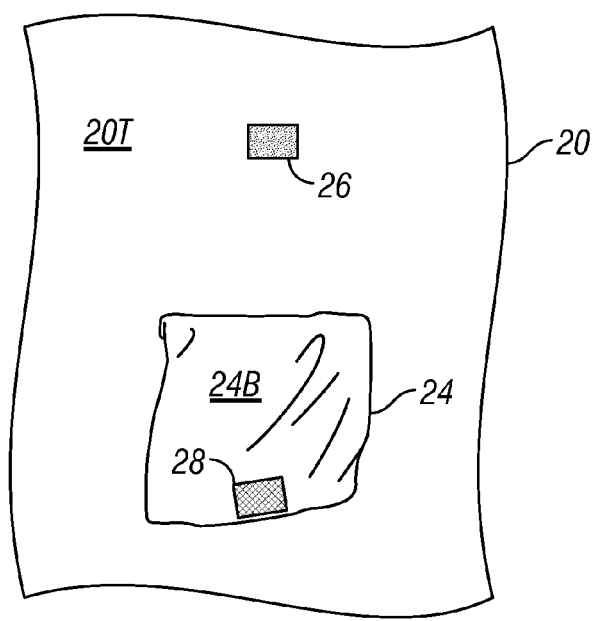
FIG. 4 is a top plan view of the top surface of the changing pad showing a protective flap closed over the hook and loop fastener.
Figure 5:
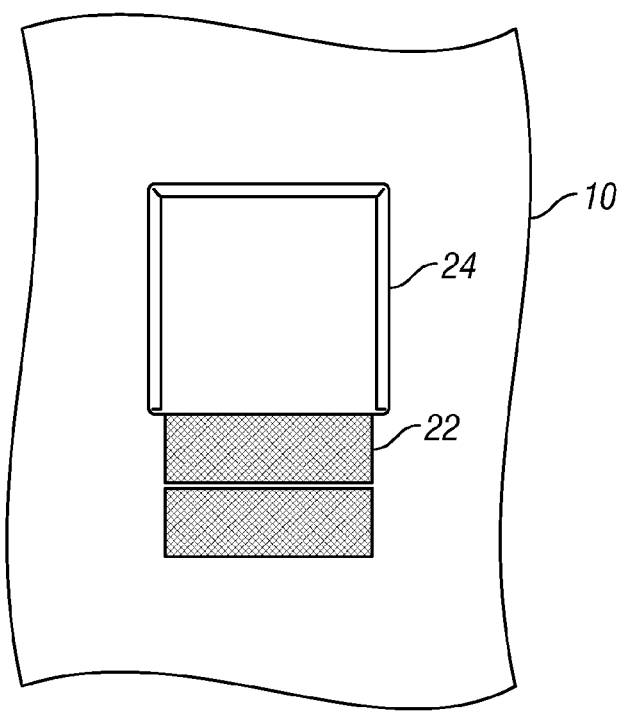
FIG. 5 is a top plan view of the top surface of the changing pad showing the protective flap open, exposing the hook and loop fastener.

FIG. 4 illustrates the flap 24 in a closed position, covering the hook and loop fastener 22 on the changing pad 20. The flap 24 has a back 24B and a front. In the closed position, the front faces the changing pad 20. On the back is a hook and loop tab 28 of hook and loop fastener material. The changing pad 20 has a hook and loop tab 26 of hook and loop fastener material. The flap 24 prevents other items, such as regular clothing, from snagging and sticking to the hook and loop fastener 22 on the surface 20T of the changing pad 20. When the user wants to use employ the diaper changing system, the user attaches the hook and loop tab 28 on the back of the flap 24 to the hook and loop tab 26 on the changing pad 20. FIG. 5 demonstrates the flap 24 attached to the changing pad 20, with the hook and loop fasteners 22 that attach to the vest 30 exposed.

Figure 6:
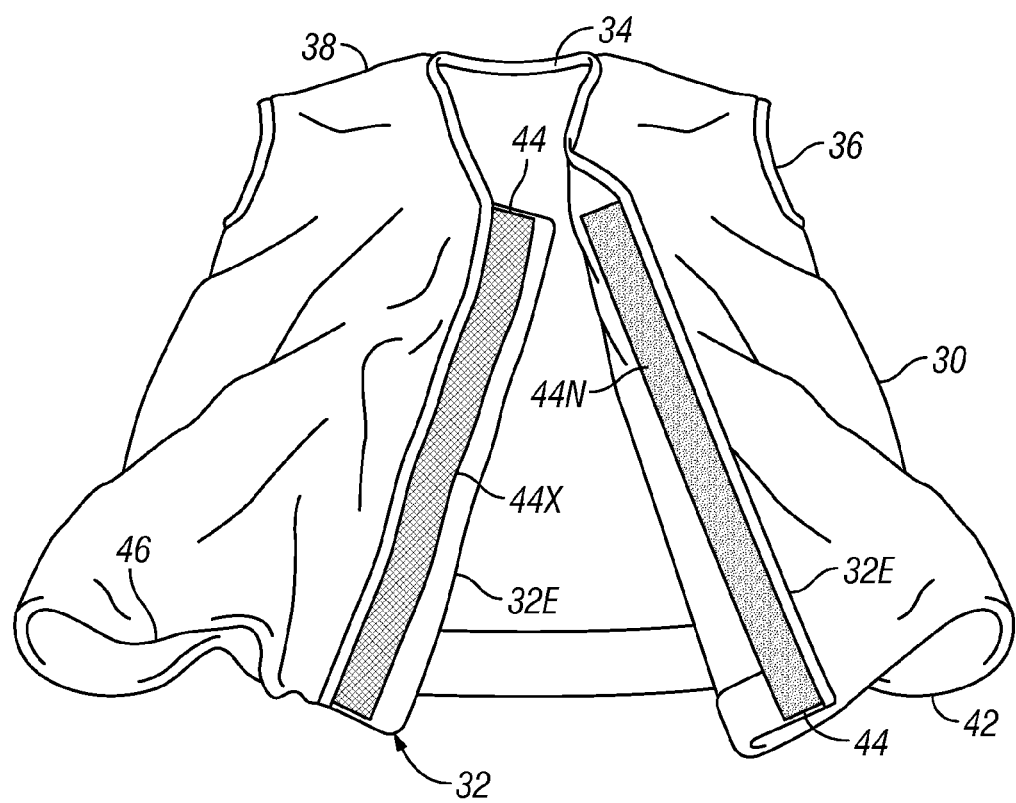
FIG. 6 is a diagrammatic perspective view of the vest from the front showing the hook and loop closure on the vest.

FIG. 6 shows the vest 30. The front opening 32 of the vest 30 has a pair of edges 32E and the vest 30 has a bottom 46, an inside and an outside. The front opening 32 has a closure formed by a pair of hook and loop fastener strips 44, one each adjacent to the pair of edges 32E, one on the inside 44N of the edge 32E, the other on the outside 44X of the edge 32E, longitudinally extending from the neck opening 34 to the bottom 46 of the vest 30. To close the front opening 32, the hook and loop strip on the inside edge is attached to the hook and loop strip on the outside edge. In the illustration, the strips are continuous, however, it is well understood by those of ordinary skill that variations in the closure, such as segmented hook and loop strips and snaps, while adhering to the inventive concept.

Figure 7:
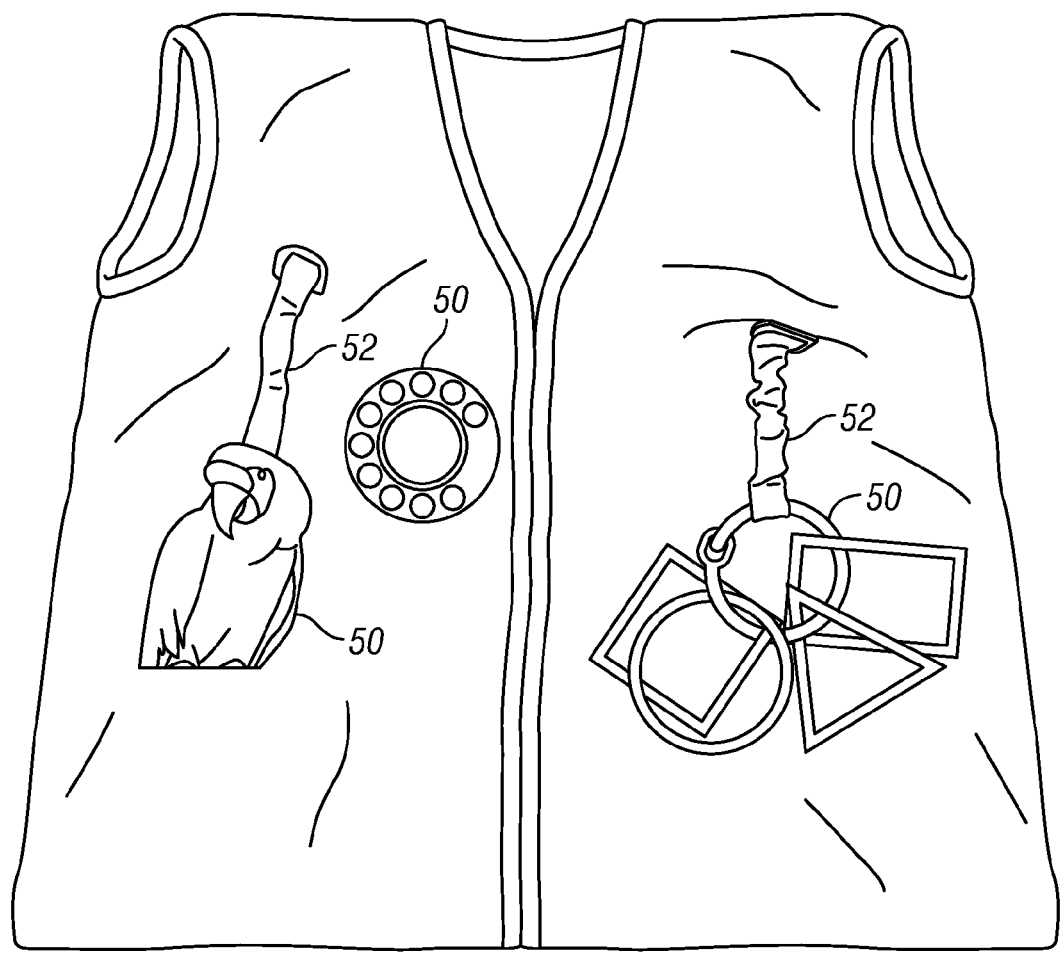
FIG. 7 is a top plan view of the closed vest from the front, showing attached toys.

FIG. 7 shows the vest with a variety of toys 50 attached to the front of the vest to amuse and distract the infant during diaper change and make wearing the vest more desirable for the infant. Some toys 50 are on a short tether 52 to avoid a strangulation hazard. This disclosure uses the term infant to describe a young child in the early period of life from infancy through toddlerhood, generally up through three years of age who is not toilet trained and wears diapers, but is capable of self-movement, such as squirming, rolling over, twisting, crawling, sitting up, or walking.

To use the system 10, as illustrated in FIG. 1, the user places the vest 30 on the infant, having a body with a pair of arms, a neck, a chest, and a back. The infant can be in a variety of positions such as standing, sitting, laying prone or laying supine. The user opens the closure 44 on the front 38 of the vest 30, and places the infant's arm into the arm openings 36, one in each opening. The user closes the closure over the infant's chest, by connecting the pair of hook and loop strips on the edges of the front opening 32. The infant need not be close to the changing pad 20 when the vest 30 is placed on the child in anticipation of a diaper change and can wear the vest routinely if playing in an upright, unsupported position.

The user opens the flap 24 on the changing pad 20 and mates the hook and loop tab 28 on the flap 24 to the hook and loop tab 26 on the changing pad 20. The user places the infant on his or her back on the changing table, mating the hook and loop fastener 40 on the rear 42 of the vest 30 to the hook and loop fastener 22 on the surface 20T of the changing pad 20. The infant is safely and securely restrained from rolling over, twisting and rolling off the pad. The infant can play with the toys 50, shown in FIG. 7, tethered to the front of the vest. After the diaper is changed or the user finishes a procedure that required the child to be restrained, the user may lift the child off the changing pad 20, disengaging the mated hook and loop fasteners 22, 40 on the vest 30 and the changing pad 20, as shown in FIG. 2. The flap 24 is closed to cover the hook and loop fastener 22 on the changing pad 20 by disengaging the hook and loop tabs 26, 28 on the flap 24 and changing pad 20. Referring to FIG. 1, alternatively, the user can open the front closure of the vest 30, lift the infant out of the vest 30, leaving the vest 30 attached to the changing pad 20. When the user next requires the system 10 to change a diaper, the user can either place the infant in the vest 30 by laying the infant down on the open vest 30, placing the arms through the arm openings 36 and closing the front opening. In another variation, the user can remove the vest 30 from the changing pad 20 and place it on the infant by following the steps discussed hereinabove before laying the infant on the changing pad 20.

In one embodiment, the vest is made of cloth. In another embodiment, the vest is made of plastic, such as vinyl or polymer blends for sponge bathing the child on the changing pad. The changing pad in this system is made of plastic, such as for example, but not limited to, vinyl with the hook and loop fasteners attached to the surface or the changing pad has a removable plastic or cloth liner with the hook and loop fasteners attached to the surface of the removable liner. The removable liner can be employed on a wide variety of horizontal surfaces that are used for changing diapers.

In conclusion, herein is presented a system to securely hold an infant on a changing pad while changing a diaper. The invention is illustrated by example in the drawing figures, and throughout the written description. It should be understood that numerous variations are possible, while adhering to the inventive concept. Such variations are contemplated as being a part of the present invention.

What is claimed is:

1. A method of changing a diaper using a system to securely hold a toddler with a pair of arms and a torso having a back and a chest and wearing a diaper and a vest, the vest having a rear, a pair of arm openings and a front, the front having an opening with a closure, the rear having a first hook and loop fastener, on a changing pad with a top surface having a second hook and loop fastener fixed on the top surface, comprising:

placing the vest on the torso of the toddler by placing the pair of arms of the toddler through the arm openings of the vest, the rear of the vest on the back of the toddler and the front of the vest on the chest;

securing the front opening secured with the closure after placing on the toddler;

laying the toddler down supine on the changing pad;

attaching the second hook and loop fastener fixed on the top surface of the changing pad to the first hook and loop fastener on the rear of the vest; and changing the diaper while the toddler is held securely on the changing pad by the vest, wherein the changing pad has a hook and loop tab and the step of laying the toddler down on the changing pad is preceded by the step of opening a flap on the changing pad covering the second hook and loop fastener on the top surface of the changing pad, the flap having a hook and loop tab on the back of the flap, the hook and loop tab on the back attaching to the hook and loop tab on the changing pad, maintaining the flap open.

2. The method of changing a diaper using a system to securely hold a toddler as described in claim 1, wherein the steps as recited are followed by the steps of removing the toddler wearing the vest from the changing pad by detaching the first hook and loop fastener from the second hook and loop fastener and closing the flap on the changing pad to cover the hook and loop fastener on the top surface of the changing pad.

3. The method of changing a diaper using a system to securely hold a toddler as described in claim 2, wherein when the vest is placed on the torso of the toddler, the vest is unattached to the changing pad and the toddler is in an upright position.

4. The method of changing a diaper using a system to securely hold a toddler as described in claim 3, wherein the vest is placed on the toddler immediately before diaper changing.

* * * * *